US00PP13175P2

(12) United States Plant Patent
Howard

(10) Patent No.: US PP13,175 P2
(45) Date of Patent: Nov. 5, 2002

(54) PEACH TREE NAMED 'AGRIPEACHONE'

(75) Inventor: George Howard, Selma, CA (US)

(73) Assignee: Agri Sun Nursery L.L.C., Selma, CA (US)

( * ) Notice: Subject to any disclaimer, the term of this patent is extended or adjusted under 35 U.S.C. 154(b) by 8 days.

(21) Appl. No.: 09/603,909

(22) Filed: Jun. 26, 2000

(51) Int. Cl.[7] ..... A01H 5/00

(52) U.S. Cl. ..... Plt./195

(58) Field of Search ..... Plt./195, 194

(56) References Cited

U.S. PATENT DOCUMENTS

PP5,123 P * 10/1983 Bailey et al. ..... Plt./196

* cited by examiner

*Primary Examiner*—Bruce R. Campell
*Assistant Examiner*—W C Baker
(74) *Attorney, Agent, or Firm*—Burns, Doane, Swecker & Mathis, LLP

(57) ABSTRACT

A new and distinct mid-season peach tree cultivar (i.e., *Prunus persica*) is provided that forms attractive highly blushed vertically flattened fruit. The fruit has semi-freestone white flesh that is sweet and juicy and of low acid content. The fruit commonly is larger and possesses slightly more red blush than the 'N.J. F-2' cultivar (U.S. Plant Pat. No. 5,123). Also, the fruit commonly matures at least three weeks later than the 'N.J. F-2' cultivar.

3 Drawing Sheets

SUMMARY OF THE INVENTION

Figure 1:
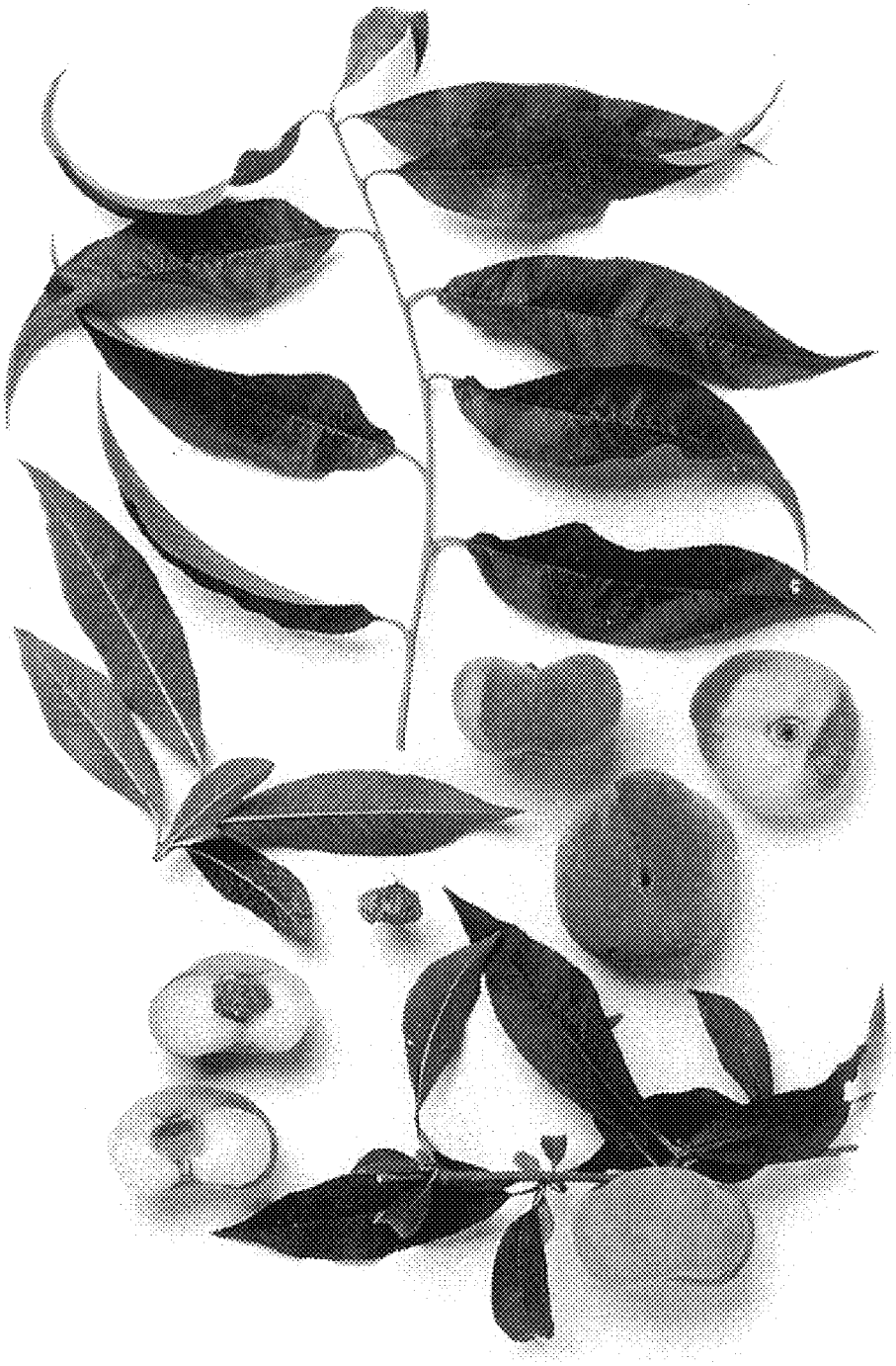

The present invention is directed to a new and distinct peach (i.e., *Prunus persica*) cultivar that originated as a chance seedling on the property of Agri Sun Nursery L.L.C. located at Selma, Calif. The peach seed used in the planting was harvested from an open-pollinated tree of the 'N.J. F-2' cultivar (U.S. Plant Pat. No. 5,123). The pollen parent (i.e., the male parent) is unknown.

The seed that produced the new cultivar of the present invention was planted in the late fall and winter of 1993. The first fruit was observed during 1995 and 1996. Had my efforts including the growing and study of the seedlings not have led to the discovery and preservation of the new cultivar of the present invention, it would have been lost to mankind.

It was found that the new peach cultivar of the present invention exhibits the following combination of characteristics:

(a) Forms highly blushed fruit having a vertically compressed oblate configuration, (b) Forms fruit having semi-freestone white flesh that is sweet and juicy with a low acid content, (c) The fruit commonly is larger and possesses slightly more red blush than the 'N.J. F-2' cultivar, and (d) The fruit commonly matures at least eighteen to twenty-one days later than the 'N.J. F-2' cultivar.

The flattened configuration of the fruit is somewhat unusual. It is understood that peaches of this shape were discovered in China over 3,000 years ago, and are believed to have been introduced into the United States from Spain. In the early 1800's peaches of this general configuration are reported to have been grown by early settlers in the Midwest.

The new cultivar of the present invention exhibits a mid-season harvest date. The white flesh is crisp at harvest and can be classified as being semi-freestone since it breaks away easily from the pit. The skin is mostly dark red with some yellow. More red coloration is present with increasing exposure to sun during maturation. The crisp nature of the fruit at harvest enables it to ship well and to well tolerate routine handling procedures. The fruit also holds up well in storage and displays a good shelf life. The flavor at harvest is very good and possesses a very low acid level.

The new variety of the present invention readily can be distinguished from its maternal parent (i.e., the 'N.J. F-2' cultivar) by its substantially later maturity date, larger fruit, slightly more red blush on the fruit skin, and very sweet low acid flavor.

Asexual reproduction by budding at Selma, Calif., has demonstrated that the characteristics of the new cultivar are firmly fixed and are reliably transferred from one generation to another. Budwood was first collected from the original seedling of the new cultivar during the winter of 1996. Seedlings were budded early in the spring of 1997. The fruit was first observed on the resulting trees in July of 1998. The characteristics of the new cultivar were consistently displayed in the subsequent generation following such asexual propagation.

The new cultivar of present invention has been named 'AgriPeachOne' and is being commercially marketed under the JUPITER trademark.

BRIEF DESCRIPTION OF THE PHOTOGRAPHS

The accompanying photographs show specimens of various plant parts of the new cultivar in color as nearly true as it is possible to make the same in color illustrations of this character. The plants were grown at Selma, Calif.

FIG. 1 illustrates specimens of the fruit and foliage during late July 1999 as the fruit approached maturity. The illustrated fruit having a vertically compressed oblate configuration was produced under growing conditions that experienced some shading during fruit maturation. Accordingly less red blush has developed than if the fruit had experienced more exposure to sun. Also, the red-brown coloration of the illustrated stone is the result of some darkening due to the exposure to air.

Figure 2:
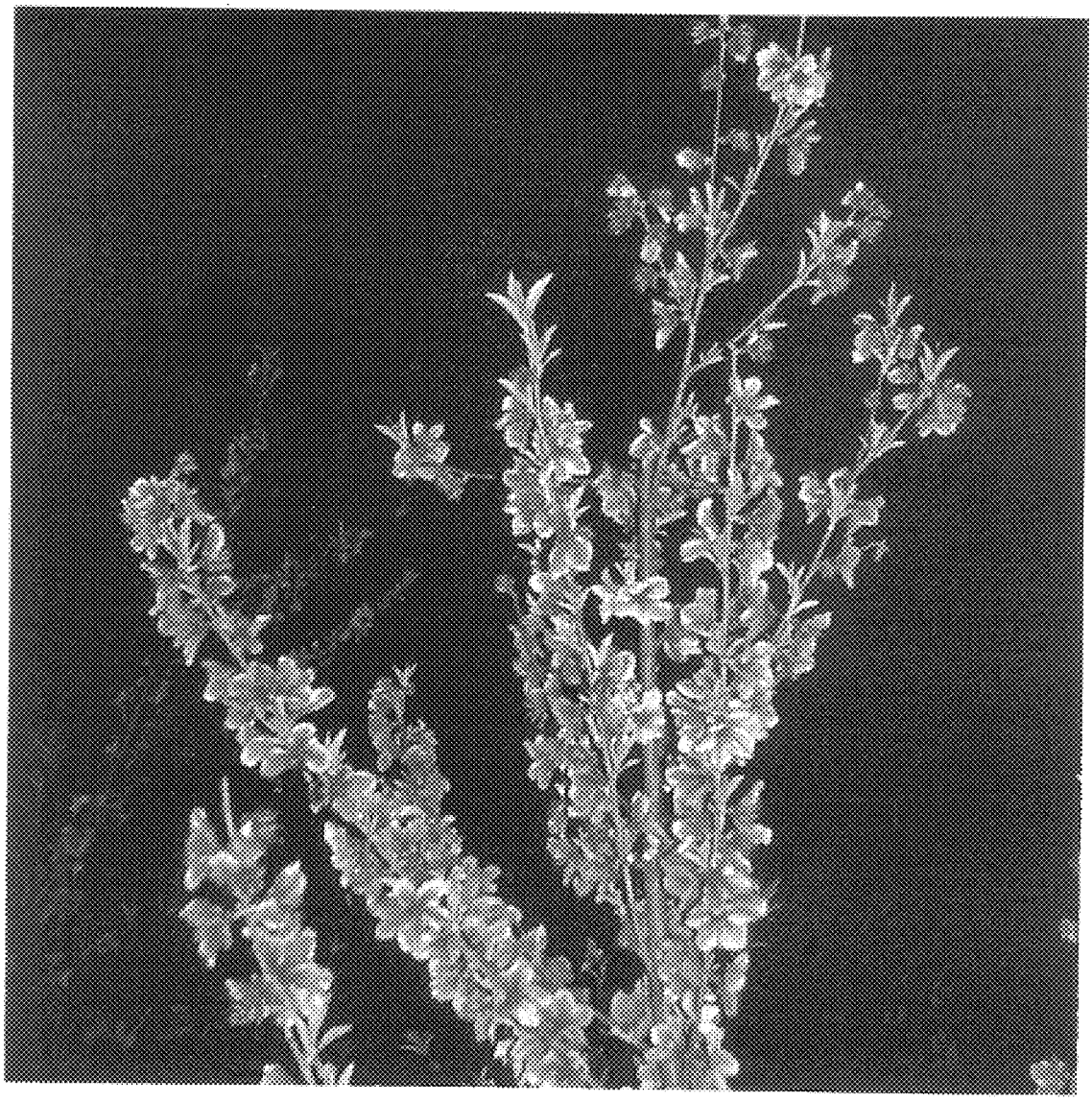

FIG. 2 illustrates specimens of the large showy blossoms during March 2001. The illustrated blossoms are in various stages of opening. It will be seen that the petal margins exhibit more lightening in coloration with age.

Figure 3:
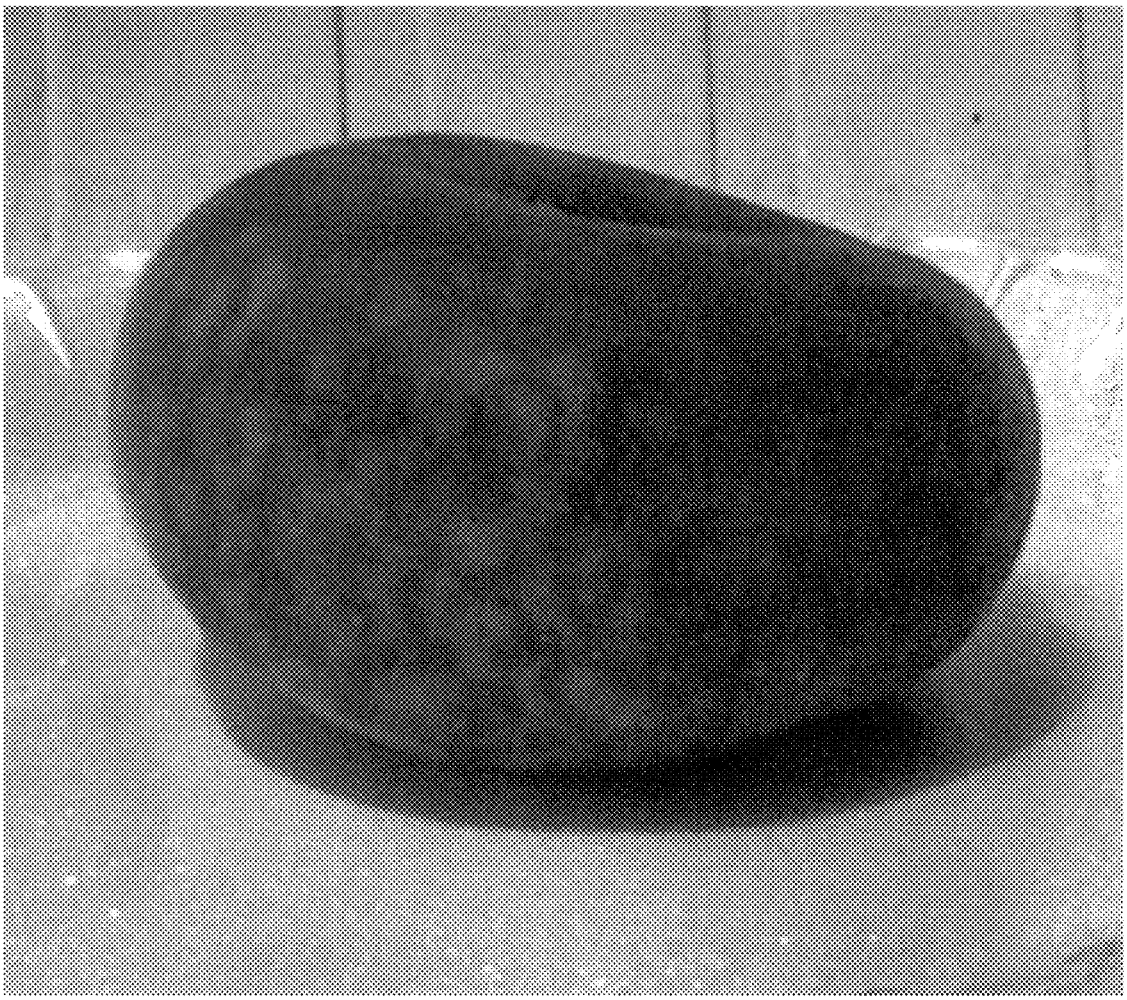

FIG. 3 illustrates a typical fruit during July 2000. The illustrated fruit was produced on a young tree of approximately four years of age and experienced more exposure to sun during maturation than the fruit illustrated in FIG. 1. Accordingly, the illustrated fruit exhibits more red coloration.

DETAILED DESCRIPTION

The following detailed description of the new cultivar was obtained through the observation of plants growing at Selma, Calif. The observed plants were approximately four years of age, and were grown on Nemaguard rootstock in the field under typical soil and weather condtions for the area. Color designations are with reference to the Color Name Chart of the Inter-Society Color Council, National Bureau of Standards. Common color terms are to be accorded there customary dictionary significance.

Botanical classification: *Prunus persica*, cv. 'AgriPeachOne'.

Tree:

*Size.*—Generally comparable to the 'N.J. F-2' cultivar depending on the nature of shaping and pruning. For instance a four year-old tree with commercial pruning when grown at a spacing of 10×16 feet commonly will exhibit a height of approximately 9 to 10 feet and a width of approximately 6 to 7 feet.

*Vigor.*—Very vigorous and generally comparable to that of the 'N.J. F-2' cultivar.

*Productivity.*—Very good.

*Regularity of bearing.*—Reliably bears a crop each year.

*Trunk.*—Diameter: Generally comparable to that of the 'N.J. F-2' cultivar. The diameter will vary with spacing and other cultural conditions. At the age of three years using semi-high density planting of 10×16 feet the diameter commonly is approximately 2.5 to 3 inches. Trunk diameters are larger when the trees are spaced farther apart. Surface characteristics: semi-rough and generally comparable to the 'N.J. F-2' cultivar, and commonly with approximately 10 to 14 lenticles per square inch. Lenticels: commonly approximately ⅛ inch in length, and the coloration is 51 deep 0. Bark color: light brown (57 l. Br.).

Branches:

*Size.*—Typical for peach trees and depending on the nature of shaping and pruning.

*Surface characertistics.*—Semi-rough and generally comparable to that of the 'N.J. F-2' cultivar.

*Color.*—Light brown (57 l. Br.).

*Lenticels.*—Small to medium in size, commonly aprproximately ⅛ inch in length, commonly present in a frequency of approximately 10 to 14 per square inch, and 51 deep 0 in coloration.

*Crotch angles.*—Commonly approximately 40 to 50 degrees, and can be modified to approximately 70 to 75 degrees with supports.

Leaves:

*Size.*—Commonly approximately 4½ to 6½ inches in length and approximately 1½ to 2 inches in width.

*Configuration.*—Lanceolate, and more elongated than typical of peach trees. The tip is pointed and the base is cuneate.

*Color.*—Dark green (137 d.y. G) on the upper surface and light green (136 m.y. G) on the under surface.

*Texture.*—Smooth upper surface and light pubescence on the under surface.

*Margins.*—Serrate.

*Petioles.*—Commonly approximately 7/16 inch in length and approximately 1/16 inch in thickness.

*Stem glands.*—Number: commonly one pair per petiole when present. Size: very small. Configuration: reniform. Color: dark-green (125 m. ol. G).

Flower buds (observed as pink starts to show at apex of the bud):

*Size.*—Commonly approximately ¼ inch in diameter and approximately ¼ inch in length.

*Petiole.*—Commonly approximately ⅛ inch in length.

*Configuration.*—Substantially round.

*Color.*—Dark red (17 v.d. Red) with some light red (11 v. Red) at the apex.

Flowers:

*Date of bloom.*—Approximately March $1^{st}$ to $10^{th}$ at Selma, Calif., and substantially the same as the 'N.J. F-2' cultivar.

*General apperance.*—Large and showy.

*Flower shape.*—Typical of peach trees.

*Petal number.*—Five.

*Petal size.*—Approximately ¾ inch in length and 11/16 inch in width.

*Color.*—Darker red when first open than the 'N.J. F-2' cultivar, then lightens with age. Very light pink (4.1 pink) commonly is displayed. The petal margins commonly exhibit more lightening with age as shown in FIG. 2 while a darker pink remains at the center of the petals.

*Configuration.*—Sightly elongated.

*Stem length.*—Commonly approximately ⅛ inch.

*General appearance.*—Large, light pink blossoms.

Fruit:

*Date of maturity.*—Commonly mid-July at Selma, Calif., and commonly at least 18 to 21 days after the 'N.J. F-2' cultivar. Representative dates during 2001 are July $6^{th}$ for the present cultivar and June $18^{th}$ for the 'N.J. F-2' cultivar at Selma, Calif.

*Configuration.*—Round, and vertically flattened.

*Uniformity.*—Very good.

*Size.*—Commonly approximately 2½ to 3 inches in diameter, and approximately 1⅜ to 1⅝ inch in thickness. The size tends to be larger in circumference than that of the 'N.J. F-2' cultivar.

*Suture.*—Smooth, and the length from the base to the apex commonly is approximately 2½ to 3 inches.

*Stem cavity.*—Commonly substantially round, and approximately 3/16 inch in depth.

*Base.*—Flat and rounded.

*Apex.*—The apex lacks a point and commonly includes a recessed area of approximately 3/16 inch.

Fruit stem:

*Length.*—Commonly approximately ¼ inch.

*Diameter.*—Commonly approximately ¼ inch.

Fruit skin:

*Thickness.*—Typical for a peach, pubescent, tough similar to that of the 'N.J. F-2' cultivar, and tenacious to the flesh.

*Color.*—Mostly dark red (17 v.d. Red) with some light red (3 d. Pink) and yellow (98 brill g.Y) with more darker red surface than the 'N.J. F-2' cultivar. Maximum red coloration occurs when the trees are planted less densely and the fruit is more exposed to the sun.

*Tendency to crack.*—None.

*Pubescence.*—Very light (as illustrated).

Fruit flesh:

*Color.*—White (263 white).

*Surface of pit cavity.*—Flesh somewhat tight to the pit due to the rough nature of the pit.

*Juice.*—Medium juicy.

*Aroma.*—Slight.

*Fibers.*—None present.

*Flavor.*—Mild and low acid.

*Ripening.*—Substantially even throughout.

*Eating quality.*—Very mild and low acid taste.

Stone:

*Degree of freedom.*—Semi-freestone, the flesh is tight to the stone but does break free from the flesh.

*Fibers.*—None present.

*Size.*—Commonly approximately 5/8 inch in length, and approximately 7/8 inch in width.

*Color.*—Red (11 v. Red). The coloration darkens upon exposure to air.

*Form.*—Substantially round and flat.

*Base.*—Rounded and flat and approximately 1/4 inch in diameter.

*Apex.*—Flat.

*Sides.*—Very rough.

*Ridges.*—Light and commonly approximately 1/32 to 1/16 inch in depth.

*Tendency to split.*—None.

Vigor: Very vigorous and generally comparable to that of the 'N.J. F-2' cultivar.

Chilling: The chilling requirement is similar to that of the 'N.J. F-2' cultivar, and is believed to be approximately 600 to 1,000 hours. The buds exhibit exceptional cold hardiness similar to those of the 'N.J. F-2' cultivar.

Productivity: Estimated to be approximately 8,000 pounds per Acre on three year-old trees planted at a spacing of 10×16 feet.

Use: Fresh market.

Keeping quality: Keeps approximately 7 to 10 days at room temperature and has kept in excess of three weeks in cold storage.

Shipping quality: Good. Has kept on shelf 7 to 10 days. Handles and ships well due to very firm nature.

Although the new 'AgriPeachOne' cultivar of peach tree possesses the above-described characteristics as a result of the growing conditions at Selma, Calif., it is to be expected that variations of the usual type and magnitude may appear that are caused by differences in growing conditions, fertilization, pruning, pest control and other horticultural practices when the new cultivar is grown in different environments.

I claim:

1. A new and distinct cultivar of peach tree that exhibits the following combination of characteristics:

(a) Forms highly red blushed fruit having a vertically compressed oblate configuration, (b) Forms fruit having semi-freestone white flesh that is sweet and juicy with a low acid content, (c) The fruit commonly is larger and possesses slightly more red blush than the 'N.J. F-2' cultivar, and (d) The fruit commonly matures at least eighteen to twenty-one days later than the 'N.J. F-2' cultivar;

substantially as shown and described.

* * * * *